United States Patent [19]

Hofer

[11] 4,214,059
[45] Jul. 22, 1980

[54] METHOD FOR THE PRODUCTION OF IODOPHOR POWDERS

[75] Inventor: Peter Hofer, Liestal, Switzerland

[73] Assignee: The Purdue Frederick Company, New York, N.Y.

[21] Appl. No.: 914,683

[22] Filed: Jun. 12, 1978

[51] Int. Cl.$^2$ .................. A01N 11/00; C08F 8/22
[52] U.S. Cl. ..................... 525/356; 260/17.4 ST; 260/DIG. 47; 424/80; 424/150
[58] Field of Search ............. 260/17.4 ST, DIG. 47; 424/80, 150; 526/43, 44, 45; 525/356

[56] References Cited

U.S. PATENT DOCUMENTS

| | | | |
|---|---|---|---|
| 2,706,701 | 4/1955 | Beller et al. | 424/80 |
| 2,739,922 | 3/1956 | Shelanski | 424/80 |
| 2,900,305 | 8/1959 | Siggia | 424/80 |
| 4,017,407 | 4/1977 | Cantor et al. | 424/80 |
| 4,038,476 | 7/1977 | Atasoy et al. | 424/80 |

FOREIGN PATENT DOCUMENTS 2553683  8/1976  Fed. Rep. of Germany ............ 424/80

*Primary Examiner*—Stanford M. Levin
*Attorney, Agent, or Firm*—Steinberg & Blake

[57] ABSTRACT

Iodophor powders are prepared by suspending a particulate iodophor-forming polymer in an iodine solution in which the polymer is insoluble, and adding to the suspension a solution of an iodide in a solvent system miscible with the solvent of the iodine solution, to cause the formation of an iodophor. The iodophor can be separated from the solvent by filtration.

11 Claims, No Drawings

METHOD FOR THE PRODUCTION OF IODOPHOR POWDERS

BACKGROUND OF THE INVENTION

Iodophor compounds are well known germicidal agents comprising the combination of iodine with an organic carrier, particularly povidone, as well as cationic and anionic and nonionic detergents. In 1965 Beller and Hosmer (U.S. Pat. No. 2,706,701) and in 1956 Shelanski (U.S. Pat. No. 2,739,922) disclosed processes for the production of polyvinylpyrrolidoneiodine (PVP-I) by either dry mixing of the PVP and the iodine at 90°–100° C., or by preparing solutions of both resulting in an iodophor with reduced iodine toxicity and without iodine vapor. It was claimed in these patents that stability is reached after the formation of an iodine to iodide ratio of 2:1.

In 1959, Siggia (U.S. Pat. No. 2,900,305) described an improvement in the dry mixing process in which PVP with about 10% of water was used. Cantor et al (U.S. Pat. No. 4,017,407) and Atasoy et al. (U.S. Pat. No. 4,038,476) recently reported the use of PVP-iodide in place of PVP for faster dissolution of the iodine in PVP solution or in dry mixing.

SUMMARY OF THE INVENTION

Generally speaking, in accordance with the present invention, an organic iodophor-forming compound or compounds is suspended in a solution of iodine in a solvent in which the iodophor-forming compound is insoluble after which a solution of an iodide in a solvent system miscible with the solvent of the iodine solution is slowly added until the iodine solution becomes colorless. This causes the iodophor-forming compound to become bound to the iodine, thus forming a homogeneous iodophor powder.

For completion of double bond iodination, the powder may be heated up to 100° C. unitl solutions in water show constant amounts of available iodine, preferably 0.5–1%. The percentage of available iodine in the powder may reach up to 25%, preferred being 5–20%.

The use of iodine in solution greatly speeds the complexation with the iodophor-forming compound while at the same time, the use of solid iodophor avoids the need for an extra drying step, e.g. spray drying, and still further, the initial addition of appropriate amounts of iodide prevents the formation of iodine vapors from starting so that the overall process is a simple, clean reaction compared to the previous processes. Still further, the initial solvent for the iodine can be recycled after washing with water.

The process of the present invention is applicable to the use of all organic iodophor-forming compounds which include the various surfactant compounds such as poloxamer, as well as various non-surfactant compounds such as PVP.

PVP, which is the abbreviation for polyvinylpyrrolidone, which is also known as "povidone" is generally considered to be the most useful of the iodophor-forming compounds, and the method of this invention is particularly applicable thereto. However, the method of the present invention may also be applied to the preparation of other iodophor complexes which comprise the non-ionic, cationic and anionic detergent carriers.

The non-ionic surface active agents include, for example, the non-ionic polyglycol ether type surface active agents which are obtained by condensing alkylene oxides with waterinsoluble organic compounds containing at least 6 carbon atoms and having an active hydrogen, such as organic hydroxy compounds, i.e., alcohols, phenols, thiophene, primary and secondary amines, carboxylic and sulfonic acids and their amides. Nonionic polyglycol ether type surface active agents of this class are well known in the art and are disclosed, together with methods for their preparation in U.S. Pat. Nos. 1,970,578 and 2,213,477. These agents may be represented by the general formula:

wherein R represents the residue of organic compound containing an active hydrogen and R' represents hydrogen or lower alkyl and 'n' represents an integer of from 3 to 100 or higher, but usually from 6 to 50. These compounds are readily obtained by the methods disclosed in the above mentioned patents by condensing a polyglycol ether containing the required number of alkyleneoxy groups, or an alkylene oxide, usually ethylene oxide, propylene oxide or butylene oxide, with a water-insoluble organic compound containing at least 6 carbon atoms and having an active hydrogen, as for example an alkylphenol.

Other members of the group of non-ionic surfactants also may be used in this new process to prepare iodophors as for example, the class of non-ionic surfactants characterized by the condensation of polyoxypropylenegycol with ethylene oxide containing various chain lengths. Such non-ionic agents are disclosed and claimed in U.S. Pat. No. 2,674,619 and have the general formula:

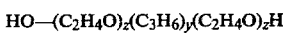

wherein Y equals at least 15; and $(C_2H_4)$ $z+z'$ equals 20–90 percent of the total weight of the compound. These non-ionic surface active agents are available commercially and known by the trade name Pluronics, a product of Wyandotte chemicals Corporation of Wyandotte, Michigan.

Among the suitable anionic surface active agents which can be used for the formation of iodophors in accordance with the present invention are those represented by the formula:

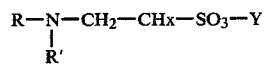

wherein R is the radical $C_xH (2x+1) CO$; x being an interger of from 5 to 17 and R is selected from group consisting of hydrogen, ($C_1$–$C_4$) alkyl and cyclohexyl radicals and Y is selected from the group consisting of salt-forming cations. The preferred anionic detergent compounds are of the well known groups of anionic surface active agents known as alkanoyl taurates and alkylaryl sulfonates such as alkyl benzene sodium sulfonate and alkyl naphthyl sodium sulfonate.

Among the suitable cationic surface active agents that may be used as iodophor-forming compounds in accordance with the invention are quaternary ammonium salts such as those formed by the alkylation of fatty amines; straight chain fatty amine salts having from 8 to 18 carbon atoms in chain length, as for example, octadecyl amine; amino amides and imidazolines.

In general, the present invention will be discussed with respect to the use of PVP as the iodophor-forming compound. It is to be understood, however, that any of the other solid organic iodophor-forming compounds can be used, and in fact, mixtures can be used. The most suitable solvents for the iodine, or a mixed halogen in which the organic iodophor-forming compound, particularly PVP, is insoluble, are the saturated alkanes or halogenated alkanes, preferably with boiling points of at least 45° C.

The iodide which is added in the form of a solution in a solvent system miscible with the solvent for the iodophor-forming compound is preferably in the form of hydrogen iodide or ammonium iodide. However, any other source of iodide ion can be used, for example, potassium iodide, sodium iodide, lithium iodide, etc.

The most suitable solvent system for the iodide, that is a solvent system in which the iodide is soluble and which is miscible with the solvent for the iodine in which the iodophor-forming compound is insoluble, is a mixture of a small amount of water with a larger amount of an alkanol or alkanone. The most suitable alkanols are methanol, ethanol and propanol. Other aliphatic alcohols can be used. The preferred aliphatic ketones are acetone and 2-butanone.

The solution of the iodide in the solvent system miscible with the solvent for the iodine is added slowly to the suspension of the iodophor-former in the iodine solution, until the iodine solution becomes colorless. This generally requires about two hours. In the case of the use of PVP as the iodophor-former, simple filtration results in the obtaining of a homogeneous PVP-I powder. The use of a mixed polymer iodophor-former, such as PVP and dextran or dextranomer up to a ratio of 3 to 5 in case of 10% available iodine results in the formation of the corresponding mixed polymer iodophor powder. When using PVP, it is desirable to use a good quality PVP (K15 to K90). As indicated above, double bond iodination is completed by heating of the powder to 100° C. until solutions in water show constant amounts of available iodine.

DESCRIPTION OF PREFERRED EMBODIMENTS

The following examples are given to further illustrate the present invention. The scope of the invention is not, however, meant to be limited to the specific details of the examples.

EXAMPLE 1

8.5 g of PVP (K30) are suspended in a solution of 1.1 g of iodine in 200 ml of petroleum ether. A solution of 0.363 ml of 56% HI in 5 ml of acetone is added slowly. After 2 hr the solvent is colorless and the PVP-I collected on a filter (10.7 g). Titration with 0.01 N $Na_2S_2O_3$ solution gave 10.0% of available iodine.

EXAMPLE 2

The amount of PVP(K30) is reduced to 3.3 g and processed according to example 1. Collection gave 5.1 g of PVP-I with 20.2% of available iodine.

EXAMPLE 3

6.6 of PVP(K17) are suspended in a solution of 2.2 g of iodine in 400 ml of petroleum ether. A solution of 0.528 ml of 67% HI in 10 ml of acetone is added slowly. Collection after 2 hr gave 10.0 g of PVP-I with 19.8% of available iodine.

EXAMPLE 4

2.7 g of PVP(K30) are suspended in a solution of 1.1 g of iodine in 200 ml of petroleum ether. A solution of 0.4 g of $NH_4I$ in 0.2 ml of water and 5 ml of acetone is added slowly. Collection after 3 hr gave 4.4 g of PVP-I with 20.2% of available iodine.

EXAMPLE 5

2.3 g of PVP(K30) are suspended in a solution of 1.1 g of iodine in 200 ml of petroleum ether. A solution of 0.264 ml of 67% HI in 5 ml of acetone is added slowly. Collection after 3 hr gave 4.1 g of PVP-I with 24.6% of available iodine.

EXAMPLE 6

8.5 g of PVP(K30) are suspended in a solution of 1.41 g of iodine monochloride in 200 ml of petroleum ether. A solution of 0.264 ml of 67% HI in 5 ml of acetone is added slowly. Collection after 3 hr gave 10.2 g of PVP-ICl with 8.6% of titrateable iodine.

While the invention has been illustrated in particular with respect to the use of certain solvents and solvent systems, it is apparent that variations and modifications of the invention can be made.

What is claimed is:

1. Method of producing an iodophor powder, which comprises adding to a suspension of a powdered iodophor-forming compound in a solution of iodine dissolved in a solvent in which said iodophor-forming compound is insoluble an iodide dissolved in a solvent system miscible with said solvent for said iodine, thus causing iodine to add to said iodophor-forming compound to form the corresponding iodophor in solid form.

2. Method according to claim 1 wherein said iodide solution is added until the iodine solution is colorless, thus causing all of the iodine to be bound by said iodophor-forming compound.

3. Method according to claim 1 wherein said iodophor-forming compound is polyvinylpyrrolidone.

4. Method according to claim 2 wherein said iodophor-forming compound is polyvinylpyrrolidone.

5. Method according to claim 3 wherein said solvent for said iodine is a saturated alkane or a halogenated alkane.

6. Method according to claim 5 wherein said solvent system is water and a solvent selected from the group consisting of aliphatic alcohols and aliphatics ketones.

7. Method according to claim 6 wherein the amount of water is less than the amount of said solvent.

8. Method according to claim 1 wherein said iodide is selected from the group consisting of hydroiodic acid, ammonium iodide, lithium iodide, sodium iodide and potassium iodide.

9. Method according to claim 1 wherein the amount of iodine in relation to the amount of said iodophor-forming compound in such that the resulting iodophor contains 1-25% of available iodine.

10. Method according to claim 1 wherein said iodophor-forming compound is a mixture of polyvinylpyrrolidone and dextran or dextranomer.

11. Method according to claim 10 wherein the ratio of the polyvinylpyrrolidone to dextran or dextranomer is up to a ratio of 3:5 in the case of 10% of available iodine.

* * * * *